(12) United States Patent
Viscovitz et al.

(10) Patent No.: US 6,376,437 B2
(45) Date of Patent: Apr. 23, 2002

(54) SKIN CLEANSING COMPOSITION FOR REMOVING INK

(75) Inventors: John Viscovitz; Michael J. Dolan, both of Akron, OH (US)

(73) Assignee: Gojo Industries, Inc., Akron, OH (US)

( * ) Notice: Subject to any disclaimer, the term of this patent is extended or adjusted under 35 U.S.C. 154(b) by 0 days.

(21) Appl. No.: 09/895,671

(22) Filed: Jul. 2, 2001

Related U.S. Application Data

(63) Continuation-in-part of application No. 09/428,250, filed on Oct. 27, 1999, now Pat. No. 6,265,363.

(51) Int. Cl.⁷ .............................. C11D 7/50; C11D 9/00; C11D 9/02; C11D 9/04; A61K 7/50
(52) U.S. Cl. .................... 510/130; 510/139; 510/174
(58) Field of Search ................................ 510/130, 138, 510/139, 174

(56) References Cited

U.S. PATENT DOCUMENTS 4,850,729 A * 7/1989 Kramer et al. .............. 401/183
6,265,363 B1 * 7/2001 Viscovitz ................... 510/130

FOREIGN PATENT DOCUMENTS

FR 2 683 541 * 5/1993 ............ C09D/9/00

* cited by examiner

Primary Examiner—Yogendra N. Gupta
Assistant Examiner—John M. Petruncio
(74) Attorney, Agent, or Firm—Reese Taylor

(57) ABSTRACT

A skin cleansing composition suitable for removing ink and other stains from the hands and arms of a user includes an effective amount of a low molecular weight alcohol having from one to twelve carbon atoms and an effective amount of a peroxide releasing agent, e.g., a perborate salt, preferably sodium perborate, such that together, the alcohol and perborate salt provide a synergistic reaction that effectively removes ink from the skin of the user. Other additives such as fillers, abrasives, and detergents may be employed to provide further cleansing action.

22 Claims, No Drawings

SKIN CLEANSING COMPOSITION FOR REMOVING INK

CROSS-REFERENCE TO RELATED APPLICATIONS

This application is a continuation-in-part of U.S. Ser. No. 09/428,250, filed Oct. 27, 1999, U.S. Pat. No. 6,265,363.

TECHNICAL FIELD

The present invention relates to skin cleansing compositions containing a peroxide releasing agent and a low molecular weight alcohol, which together provide a synergistic reaction to effectively remove ink and similar stains from the skin. The peroxide releasing agent is preferably a perborate.

BACKGROUND ART

There are a number of cleansing agents and detergents which are available for different cleansing purposes. Oftentimes, however, different cleansing agents or combinations of cleansing agents must be used to cleanse different surfaces. For example, while a laundry detergent for washing clothes and the like may have many of the same or similar active ingredients as a shampoo for cleansing and conditioning the hair of a user, the active ingredients must often be used in conjunction with different non-active ingredients or in different active amounts in order to adequately protect the surface being cleaned. In other words, washing clothes with shampoo will probably not clean the clothes just as washing hair with laundry detergent could deleteriously harm the hair or scalp.

Likewise, removing ink stains from various surfaces has traditionally been a problem throughout the printing industry. There are a number of conventional ink remover solutions or compositions, but many of these can be or are known to be corrosive to the skin or otherwise harmful to the user. Attempts to improve compositions which adequately remove ink from inanimate surfaces such as screens and hard surfaces can be found throughout the patent literature, including U.S. Pat. Nos. 5,424,001 and 5,464,555, the disclosures of which are incorporated herein by reference. However, very little research has been conducted to provide a cleansing composition which will effectively cleanse the surface of the skin of the user, and more particularly, has the ability to remove ink and other tough stains from the skin, without deleteriously harming or irritating the skin, a common problem were the user to employ these other ink removing compositions capable of removing such stains from other, less delicate surfaces. To the extent that any such ink-removing skin cleansing compositions have been developed, these skin cleansing compositions typically employ either only a solvent as the active agent for removing the ink, or only a bleaching agent (without a solvent) as the active agent for removing the ink, neither of which, by themselves, are particularly effective in removing the ink.

Skin cleansing compositions are well known in the art, and are typically used to cleanse the arms and hands of the user. Some skin cleansers, such as U.S. Pat. No. 5,635,462, may be antimicrobial in nature and are used to effectively destroy bacteria and any other microorganisms which might be present on the user's arms or hands. However, the majority of skin cleansing compositions are simply employed to clean the arms and hands of the user, ridding the skin of various germs, dirt, greases, stains or other corrosive or toxic substances which might be present on the skin.

Unfortunately, at noted above, these skin cleansing compositions are not very effective in removing extremely tough stains like ink stains from the skin. Inks, particularly video jet ink or graphic ink, as used in the printing industry, are some of the toughest stains to remove from the skin. There is only one known skin cleansing composition which is capable of at least substantially removing ink stains and the like from skin. This skin cleansing composition is presently available from Stockhausen under the tradename Reduran. While the actual formulation of this product may be proprietary, it is known to comprise a reducing agent/bleach such as sodium hydrosulfite, a detergent/buffer/chelation agent such as sodium hexametaphosphate, polyethylene glycol, active cleansing agents such as cocamide DEA and cocamide MEA, kaolin, a reducing agent/solvent for dyes such as triethanolamine, a detergent/solvent/solubilizer for inks such as C12–18 Pareth 10, an abrasive such as silica filler, fragrance, and water. Other than a small amount of polyethylene glycol and water, there appears to be no solvent, e.g., alcohol, in this product.

While this composition has been effective in removing many types of inks from the skin of a user, it still has a few drawbacks. For example, a significant amount of fragrance is employed in the product in order to mask the generation of $SO_2/SO_3$ created by the product. Furthermore, using the product gives a warming sensation to the hands. Such a warming sensation, while not necessarily significant to the ability of the product to cleanse the hands, often gives the user an insecure feeling of harm being done to the hands, e.g., a burning sensation or similar irritating sensation. Consequently, the need exists for a skin cleansing composition that will effectively remove ink stains from the hands and arms of the user without providing such a warming sensation.

The present invention differs greatly from the Reduran product. The present invention uses a perborate or other peroxide releasing compound, together with a substantial amount of an alkanol having from one to twelve carbon atoms, to remove ink from the hands and arms of a user. The use of peroxide releasing compounds in cleansing compositions are also well known in the art, but have heretofore not been used to remove ink from the skin. For example, U.S. Pat. No. 4,850,729, the disclosure of which is incorporated herein by reference, teaches a decontaminating composition for decontaminating hard surfaces, clothing and personnel that have been contaminated with corrosive and/or toxic substances. The decontaminating composition is derived from a water-soluble basic salt having hydrogen peroxide of crystallization, e.g., a percarbonate, an activator for hydrogen peroxide, e.g., clay, a positively-charged phase transfer agent, e.g., a phosphonium salt, and an aqueous solution comprised of a nonvolatile alcohol, namely a polyhydric alcohol, and a surface active agent such as a detergent or surfactant. Notably, this decontaminating composition uses a water-based solution and a separate activator for hydrogen peroxide to provide its decontaminating characteristics.

U.S. Pat. No. 5,712,238, also incorporated herein by reference, discloses a multipurpose cleaning agent which is practical for cleansing the face, the hair, of the body of the user, as well as for cleaning fruits and vegetables and any of a variety of household items. This cleaning agent is made from sodium alkyl sulfate, fatty acid coconut diethanolamide, citric acid, ethylene diamine tetraacetic acid, citric acid soda, water, sodium polyoxyethylene alkyl ether sulfate, sodium carboxy methyl cellulose, sodium percarbonate, sodium tripoly phosphate, soda ash light, mirabilite, savinase 40T and celluzyme 0.7T. This composition, while using a sodium percarbonate, does not include any significant or effective amounts of alcohol as a solvent. Rather, it relies on various bleaching agents to cleanse.

Other percarbonate-based cleansing compositions have been formulated for use as a laundry treatment product (U.S. Pat. No. 5,160,654), as a household detergent (U.S. Pat. No. 5,340,496), as an automatic dishwashing detergent (U.S. Pat. No. 5,599,781), or as a cleaner for cosmetic and pharmaceutical manufacturing facilities (U.S. Pat. No. 5,445,761). None of these patents, however, include a perborate or other peroxide releasing agent and a low molecular weight aliphatic alcohol, namely, an alkanol, which together provide a skin cleansing composition capable of removing ink and other stains from the skin of a user.

Thus, the need exists for a skin cleansing composition containing a peroxide releasing agent, e.g., a perborate, and a lower molecular weight alcohol, e.g., an alkanol, which composition is suitably effective in cleansing the skin and, in particular, is effective in removing ink and other tough stains from the hands and arms of the user.

SUMMARY OF THE INVENTION

It is, therefore, a primary object of the present invention to provide a cleansing composition capable of effectively cleansing the skin of the user.

It is another object of the present invention to provide a skin cleansing composition, as above, which can effectively remove ink and other tough stains from the skin.

It is still another object of the present invention to provide a skin cleansing composition, as above, which will not be harmful or toxic to the skin and which will not significantly irritate the skin.

It is yet another object of the present invention to provide a skin cleansing composition, as above, which does not cause a warming sensation to the skin when used.

These and other objects of the present invention, as well as the advantages thereof over the known art relating to skin cleansing compositions, which will become apparent from the description to follows, are accomplished by the invention hereinafter described and claimed.

In general, and in accordance with at least one aspect of the present invention, a composition for cleansing the skin of a user is described, the composition including a low molecular weight alcohol having from 2 to 12 carbon atoms; and a peroxide releasing agent, wherein the composition includes an effective amount of both the alcohol and the peroxide releasing agent to remove ink from the skin of a user. Particularly preferred compositions include those containing an aliphatic, preferably paraffinic, alcohol and a perborate.

In accordance with at least another aspect of the present invention, a skin cleansing composition is provided which includes from about 40 to about 80 percent by weight of a low molecular weight alcohol having from 1 to 12 carbon atoms (preferably, an alkanol); from about 10 to about 20 percent by weight of a peroxide releasing agent (preferably, a perborate); from about 10 to about 40 percent by weight of at least one abrasive; and from about 1 to about 3 percent by weight of an inert filler. The low molecular weight alcohol and the peroxide releasing agent together provide a synergistic reaction to effectively remove ink from the skin of a user.

PREFERRED EMBODIMENT FOR CARRYING OUT THE INVENTION

As noted hereinabove, the present invention is directed toward a cleansing composition that will effectively cleanse and remove ink and other stains from the skin of a user. The skin cleansing composition, while strong enough to remove these tough stains, is also mild enough on the skin such that it does not cause significant skin irritation or dryness. It is also not toxic to the skin, and causes a general cooling sensation when used. It may also exhibit antiseptic properties.

The essential ingredients for such a skin cleansing composition generally include a low molecular weight alcohol and a peroxide releasing agent such as a perborate. That is, it has been discovered that the combination of a perborate or other agent and a low molecular weight, preferably aliphatic alcohol, mixed together as a skin cleansing composition, provides a synergistic reaction to effectively remove ink and similar stains from the skin without harming the skin. These ingredients, together with other additives disclosed hereinbelow, provide compositions with excellent skin cleansing properties, particularly with respect to removing ink from the skin of the user. It is believed that the peroxide releasing agent releases an active peroxide (e.g., hydrogen peroxide) which, in conjunction with the alcohol solvent, provides for improved ink removing capabilities of the composition. Consequently, it is only the combination of the peroxide releasing agent, particularly perborate, and the alcohol in the cleansing system together, not each of the ingredients individually, which provides for the effective removal of ink or other stains from the skin.

As stated above, the active ingredients necessary to cleanse the skin and remove ink therefrom are a peroxide releasing agent and a low molecular weight alcohol. One preferred agent is a perborate, although other peroxide releasing agents can be used, including persilicates and perphosphates. Any known percompound salt capable of forming a stable mixture with the alcohol in the composition can be employed. In general, the perborate salt or other percompound salt should be capable of being oxidized to release hydrogen peroxide into the system. Preferred salts include those perborates having alkali metal or alkaline earth metal cations. More preferred are sodium perborate, potassium perborate, and calcium perborate. Especially preferred is sodium perborate. Sodium perborate is an odorless, non-corrosive, white granular powder. Generally, the perborate compound can be used in conjunction with the alcohol in an effective amount to remove ink from the skin. More particularly, it is believed that amounts ranging from about 10 to about 20 percent by weight, based upon the total weight of the composition, are sufficient.

Peroxide releasing agents should be distinguished from hydrogen peroxide solutions. Hydrogen peroxide is unstable and highly reactive by itself, and solutions of hydrogen peroxide gradually deteriorate. Rapid decomposition can occur in the presence of many other substances. This deterioration or decomposition causes the solution to lose its effectiveness as a cleanser. A peroxide releasing agent, in contrast, does not release peroxide until it is needed. In the cleansing composition of the present invention, contact with ink or similar stains causes the peroxide to be released. In this way, the peroxide releasing agent allows the peroxide to be metered out and used only as needed.

A low molecular weight alcohol must also be employed in conjunction with the perborate or other percompound to provide the desired cleansing properties. Generally, any monohydric or polyhydric alcohol, preferably having between 1 and 12 carbon atoms and suitable for used as a solvent, can be employed. Unlike other skin cleansing compositions, however, there is a significant amount of alcohol present in this composition, generally on the order of about 40 to 80 percent by weight based upon the total weight of the composition. This is significantly more than other cleansing compositions, and this aids in solubilizing the ink rather than utilizing other ink removing solvents.

Particularly preferred alcohols include the lower alkanols such as ethanol or isopropanol. Essentially any paraffinic alcohol having from 2 to 12 and more preferably, from 2 to 8 carbon atoms can be employed. A particularly preferred example of a suitable alcohol an ethanol is Alcohol SDA-3C. This solvent is 95–99% ethanol. Some polyhydric alcohols such as polyethylene glycol or propylene glycol could also be used because of their low toxicity, but the use of these polyhydric alcohols do not provide the enhanced ink removal properties desired of the present invention. Still other alcohols such as ether-substituted alcohols, ester-substituted alcohols and lower volatile alcohols such as 2-octyldodecanol related compounds, e.g., isocetyl alcohols, may be employed. Again, however, these alcohols do not provide the enhanced ink removal properties desired of the present invention.

Other ink solubilizing solvents such as N-methyl-2-pyrrolidone, acetates, fatty acid esters, vegetable oils, or butlyrolactones may be optionally incorporated into the composition in amounts up to about 10 percent by weight. However, these ingredients should not react with the perborate or peroxide releasing compound utilized in the formulations of the present invention. Moreover, these solubilizing agents may also provide other benefits to the skin cleansing composition. For example, these agents may also aid in moisturizing the skin.

In addition to the alcohol solvent and the perborate, the skin cleansing composition also preferably includes a inert filler and one or more abrasives. The inert filler can be any of a number of modified clays for polar/non-polar solvents, kaolins, bentonites, etc. Preferred clays are organophillic clays such as an aluminosilicate treated clay. These clays aid in stabilization of the alcohol. Preferably, the inert filler is added to the composition in amounts ranging from about 1 to about 3 percent by weight based upon the total weight of the composition.

Any of a number of abrasives can be used in the cleansing composition of the present invention. Generally, these abrasives may be organic or inorganic, and are preferably plastic. Plastic abrasives are particularly suitable for rubbing or absorbing the skin to loosen the dirt or stains from the hands, thereby allowing the perborate/alcohol system to more effectively remove the ink from the hands of the user. Other well known abrasives suitable for use in the present invention include silica, pumice, inorganic mineral fillers or organic mineral fillers, including natural or plant-derived products such as corn cobs, nut shells, etc. Abrasive powders are also used. These materials include crushable abrasives such as perlite, inorganic minerals such as carbonates and feldspar, and other plastic powders. In a preferred embodiment, polyurethane (plastic) powder and an expanded silica abrasive (perlite) are used.

The amount of abrasive to be employed in the cleansing composition can vary greatly depending upon the characteristics and parameters of the composition desired by the manufacturer. Although no abrasives are necessary to provide the ink removing properties to the composition of the present invention, it is generally known the abrasives may be used in amounts up to 50 percent by weight or more. In the preferred embodiment, the polyurethane powder and silica powder are each added in an amount preferably ranging from about 10 to about 20 percent by weight based upon the total weight of the composition.

It will also be appreciated that the composition of the present invention does not need to include any of the conventional and well known thickeners which are not abrasives such as, for example, carbomers, cellulose gum, xantham gum and guar gum. Instead, the abrasives employed in the composition can act as the thickeners/stabilizers, and therefore, other non-abrasive thickeners are not required. Where a non-abrasive thickening agent is used, it can be any of the conventional thickeners such as hydroxypropylcellulose, polyacrylic polymers (carbomers), xantham gum, or veegum (magnesium aluminum silicates), with hydroxypropylcellulose being most preferred. When used, these thickeners are preferably employed in only minor amounts of about 0.5 percent by weight or less.

Still further, the composition of the present invention may also be devoid of certain surfactants such as ethylene oxide/propylene oxide copolymers and many alkyl sulfates.

The skin cleansing compositions may also optionally include one or more surface active agents. These surface active agents may be a detergent, a surfactant or a combination thereof. Essentially any detergent with a hydrophilic/lipophilic balance (HLB) of from 8 to 20 or more (up to 40) may be used. Examples of suitable detergents include ethoxylated and propoxylated fatty alcohols. Particularly suitable are C12–C15 ethhoxylated/propoxylated fatty alcohols. These detergents and other surface active agents may be used in amounts up to about 1 percent by weight based upon the total weight of the composition.

For optimal efficiency, the pH of the composition should be between 4 and 12, and more preferably, between 4 and 8. To adjust the pH of the composition, any acid compatible with the ingredients of the present invention can be used. Preferred acids include citric acid, lactic acid, acetic acid, glycolic acid and gluconic acid, with the first two acids being most preferred. Typically, less than 1 percent by weight of the acid(s), based upon the total weight of the composition, are used to achieve the proper pH balance.

Also for optimal efficiency, up to about 1 percent by weight of a chelating agent and/or sequestering agent may optionally be added to stabilize the alcohol-based composition against metal ion contaminants. One example of a suitable chelating agent is ethylenediaminetetraacetic acid (EDTA). This agent, and/or phosphoric acid, is usually only needed if the stability of the composition in the manufacturing vessel is questioned. Heavy metal contamination or moisture in the vessel could cause such instability, and if there is significant contamination, the vessel may have to be passivated to remove the contamination. A small amount of D-limonene might also be added as an oxygen scavenger. However, it will be appreciated that, like many of the other additives, these ingredients have no demonstrable effect on the ability of the composition to remove ink or other stains from the skin.

The skin cleansing compositions may of the present invention may further include minor but effective amounts of other conventional additives such as fragrances, color additives, opacifying agents, pearlizing agents, vitamins, antimicrobial agents, vitamins, etc. An example of a particular pearlizing agent includes, but is not necessarily limited to, ethylene glycol distearate. These additives are used in amounts which do not effect the essential nature of the composition with respect to its ink removing properties.

It will be further appreciated that the composition of the present invention preferably does not include any water, but where water is used, it is employed in amounts of 25 percent or less and, more preferably, in an amount of less than about 10 percent by weight. Moreover, the water should not materially affect the nature of the present invention.

All percents by weight indicated herein are based upon the percent active composition.

The skin cleansing compositions of the present invention are generally prepared by adding a low molecular weight alcohol such as ethanol to a vessel with a mixer. The mixer is started at moderate speed and the inert filler and stabilizer for the alcohol, preferably, an organophillic clay, is added slowly. With continued mixing, the detergent such as Plurafac D-25 is added and then, the abrasives. In the preferred embodiment, a polyurethane powder is employed as the plastic abrasive as well as crushable abrasives such as Perlite. Next, an acid such as citric acid and/or phosphoric acid in added to the mixture, followed by a perborate compound such as sodium perborate. Finally, hydroxypropylcellulose may be added and mixed slowly until all components are thoroughly mixed and the resultant mixture is essentially homogeneous.

Based upon the foregoing disclosure, it should now be apparent that the use of the composition described herein will carry out the objects set forth hereinabove. It is, therefore, to be understood that any variations evident fall within the scope of the claimed invention and thus, the selection of specific components or ingredients can be determined without necessarily departing from the spirit of the invention herein disclosed and described. The compositions of the present invention are highly effective in removing ink from the skin of the user. The invention is particular suited for use in the printing industry or where ink stains on the hands and arms of a person is customary, but is not necessarily limited thereto. The compositions of the present invention can also be used with ingredients including, but not limited to, fragrances, chelating and sequestering agents, perfumes, coloring agents, thickeners, antioxidants, emollients and the like, which do not materially affect the cleansing and ink removing nature of the composition. Any alcohol which, when added, provides a synergistic reaction with the perborate employed to effectively remove ink and other tough stains from the hands and arms of the user, is believed suitable for the present invention. Moreover, other peroxide releasing compounds can be used. Further, as noted herein, the composition need not include thickeners. Various detergents can be used. Thus, the scope of the invention shall include all modifications and variations that may fall within the scope of the attached claims.

What is claimed is:

1. A composition for cleansing ink from skin, the composition comprising:
   a low molecular weight aliphatic monohydric alcohol having from 2 to 12 carbon atoms; and
   a peroxide releasing agent, wherein the composition includes an effective amount of both the alcohol and the peroxide releasing agent to remove ink from the skin of a user.

2. The composition as set forth in claim 1, further comprising an inert filler selected from the group consisting of organophillic clays.

3. The composition as set forth in claim 1, further comprising at least one abrasive material.

4. The composition as set forth in claim 3, wherein at least one abrasive material is a plastic abrasive.

5. The composition as set forth in claim 3, wherein at least one abrasive material is an expanded silica abrasive.

6. The composition as set forth in claim 4, wherein said plastic abrasive is a polyurethane powder.

7. The composition as set forth in claim 1, wherein said aliphatic alcohol is selected from the group consisting of ethanol and isopropanol.

8. The composition as set forth in claim 1, wherein said peroxide releasing agent is a perborate.

9. The composition as set forth in claim 8, wherein said perborate is selected from the group consisting of sodium perborate, potassium perborate, and calcium perborate.

10. The composition as set forth in claim 1, further comprising a surface active agent selected from the group consisting of detergents and surfactants.

11. The composition as set forth in claim 10, wherein the surface active agent is a detergent, and said detergent is a C12–C15 ethoxylated/propoxylated fatty alcohol.

12. The composition as set forth in claim 1, further comprising a thickener, and wherein said thickener is hydroxypropyl cellulose.

13. The composition as set forth in claim 1, further comprising an effective amount of an acid to adjust the pH of the composition to between 4 and 12.

14. The composition as set forth in claim 13, wherein the acid is selected from the group consisting of citric acid, lactic acid, acetic acid, glycolic acid and gluconic acid.

15. The composition as set forth in claim 1, further comprising a softening agent selected from the group consisting of chelating agents and sequestering agents.

16. An ink-removing skin cleansing composition comprising:
   from about 40 to about 80 percent by weight of a low molecular weight aliphatic monohydric alcohol having from 1 to 12 carbon atoms;
   from about 10 to about 20 percent by weight of a peroxide releasing agent;
   from about 10 to about 40 percent by weight of at least one abrasive; and
   from about 1 to about 3 percent by weight of an inert filler,
   wherein the low molecular weight alcohol and the peroxide releasing agent together provide a synergistic reaction to effectively remove ink from the skin of a user.

17. The skin cleansing composition as set forth in claim 16, further comprising up to about 1 percent by weight of a detergent; up to about 1 percent by weight of an acid to adjust the pH of the composition; and up to about 10 percent by weight of other ingredients selected from the group consisting of moisturizers, thickners, chelating agents, sequestering agents, and water.

18. The skin cleansing composition as set forth in claim 16, wherein said peroxide releasing agent is a perborate.

19. The skin cleansing composition as set forth in claim 18, wherein said perborate is selected from the group consisting of alkali metal perborates and alkaline earth metal perborates.

20. The skin cleansing composition as set forth in claim 16, wherein said aliphatic alcohol is selected from the group consisting of ethanol and isopropanol.

21. The skin cleansing composition as set forth in claim 16, wherein said inert filler is an aluminosilicate treated clay.

22. The skin cleansing composition as set forth in claim 16, wherein said at least one abrasive are selected from the group consisting of plastic abrasives, pumice, inorganic mineral fillers, organic mineral fillers, natural plant-derived abrasives, and expanded silica abrasives.

* * * * *